United States Patent
Russo et al.

(10) Patent No.: US 10,281,406 B1
(45) Date of Patent: *May 7, 2019

(54) METHOD FOR ELEMENTAL ANALYSIS IN A PRODUCTION LINE

(71) Applicant: Applied Spectra, Inc., Fremont, CA (US)

(72) Inventors: Richard E. Russo, Walnut Creek, CA (US); Jong Hyun Yoo, Dublin, CA (US); Chunyi Liu, Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/864,844

(22) Filed: Sep. 24, 2015

Related U.S. Application Data

(60) Provisional application No. 62/056,436, filed on Sep. 26, 2014.

(51) Int. Cl.
| | |
|---|---|
| *G01N 21/71* | (2006.01) |
| *G01N 33/02* | (2006.01) |
| *G01J 3/443* | (2006.01) |
| *G01N 21/85* | (2006.01) |
| *G01N 21/84* | (2006.01) |

(52) U.S. Cl.
CPC ............ *G01N 21/718* (2013.01); *G01J 3/443* (2013.01); *G01N 21/85* (2013.01); *G01N 33/02* (2013.01); *G01N 2021/845* (2013.01)

(58) Field of Classification Search
None
See application file for complete search history.

(56) References Cited

U.S. PATENT DOCUMENTS

| | | | | |
|---|---|---|---|---|
| 9,036,146 | B2 * | 5/2015 | Day ........................ | G01J 3/443 356/318 |
| 9,726,611 | B2 * | 8/2017 | Nakagawa .............. | G01J 3/443 |
| 2002/0163735 | A1 * | 11/2002 | Detlef ................ | B23K 26/0604 359/641 |
| 2008/0003339 | A1 * | 1/2008 | Johnson .................. | A23P 10/35 426/534 |
| 2012/0206722 | A1 * | 8/2012 | Grigoropoulos ...... | G01N 21/718 356/318 |
| 2014/0011690 | A1 * | 1/2014 | Dimov ............... | C12N 15/1065 506/9 |
| 2016/0178434 | A1 * | 6/2016 | Buckley ................ | G01J 3/0248 356/72 |

* cited by examiner

*Primary Examiner* — Shawn Decenzo
(74) *Attorney, Agent, or Firm* — Microtechnology Law & Analysis; Daniel L. Flamm

(57) ABSTRACT

A method and apparatus for analyzing one or more elements of targeted moving food surfaces uses laser-induced breakdown spectroscopy to detect the presence, absence, or amount of an element on a heterogeneous surface of an object, including surfaces of food products. A laser is used to quantify an element concentration without destroying the object. The method can be configured to include an automated on-line system comprising a closed-loop feedback control system operable to select a predetermined concentration.

16 Claims, 8 Drawing Sheets

WHITE LIGHT

BLUE, GREEN, YELLOW,
RED SPECTRAL EMISSION

METHOD FOR ELEMENTAL ANALYSIS IN A PRODUCTION LINE

CROSS-REFERENCES TO RELATED APPLICATIONS

This present application claims the benefit of U.S. Provisional Application No. 62/056,436 filed Sep. 26, 2014 which is hereby incorporated by reference for all purposes.

FIELD OF THE INVENTION

The present disclosure relates generally to the art of chemical analysis, and more particularly relates to improved apparatus and methods for monitoring a composition of a product using spectroscopy based on laser induced ablation.

BACKGROUND

Laser Induced Breakdown Spectroscopy (LIBS), also known as Laser Induced Plasma Spectroscopy (LIPS), is a method used for quick analysis of a sample's elementary constituents. LIBS is based on the analysis of the spectrum of light emitted by the atoms of a sample, when they are excited and ionized by a high power, short laser pulse (usually in the nanosecond range) focused on a target sample surface. A volume of the sample is vaporized and ionized to produce a plasma or spark having an elemental composition representative of the sample. The plasma, characteristic of elements present in the sample, are then collected and analyzed with a spectrometer to obtain an atomic composition. LIBS provides a fast and direct method of elemental analysis and even very small amounts (in low parts-per-million range) of an element can be detected in real time.

A number of methods have been applied to address the need for instantaneous evaluation of mineral contents on moving belt systems. There remains a need, however, for a method of analyzing the surface of a heterogeneous solid having three-dimensional substance(s) or coating(s) adhered thereto and having variable heights. There is also a need for an efficient and accurate method of on-line/real-time analysis of cooked food products having seasoning(s) or other coating(s) thereon. In particular, the method should overcome the difficulties associated with the inert properties of salt and other elements, which makes accuracy of on-line detection historically unobtainable in food applications. Such method should be reliable and cost-effective while providing for nearly instantaneous monitoring and feedback control of the food products and without negatively influencing product integrity (i.e., flavor, stability and quality). For example, such method should allow for quality control of food products prior to being packaged for consumption.

SUMMARY

The present disclosure provides a LIBS system capable of detecting, quantifying and controlling an amount of an element on the surface of a food product during movement or conveyance of the food product. One or more elements on the surface of a snack food or its entire elemental composition can also be detected, quantified and controlled in real-time using the LIBS system described herein. More specifically, by using the LIBS system described herein, the amount of coating(s) or particles applied to the surface of an object can be accurately monitored and adjusted if desired.

In one embodiment, the object of the present disclosure is therefore to provide a method and apparatus that permit reliable, non-destructive analysis of a food product by focusing a laser pulse onto the surface of a food. The embodiment also provides a means for direct monitoring of ready-to-eat foods with a LIBS system, while overcoming interferences such as those associated with oils on cooked foods or within the environment and the presence of small three-dimensional particles on the surface, thereby achieving continuous LIBS analysis on or above a moving product line. The invention may also use a series of laser pulses and signal processing to analyze an elemental composition of the surface and by such means permit simultaneous analysis and control of multiple elements on the surface, including without limitation seasoning particles or coating(s). A regression method can be used to correlate a percentage concentration with a wavelength unique to an element.

In one aspect, the method and apparatus of the present disclosure identifies and quantitates an element or elemental composition at different heights and sample presentations, using a laser configuration without affecting food product stability or quality.

In one aspect, the present disclosure provides for the direct and real-time monitoring of food samples being moved or conveyed on a carrying medium.

In another aspect, the present disclosure relates to a method and apparatus for coupling an elemental analysis system based on LIBS to the surface of a food product without negatively influencing or affecting the integrity, taste, appearance or texture of the food product. In particular, ready-to-eat snack food product having been cooked and seasoned are analyzed using LIBS system without negative impact on the final product ready for consumption by a consumer. Thus, the present disclosure addresses the problem of analyzing a non-homogenous (or heterogeneous) food product; or more specifically, a cooked (oil-containing) snack food product having small particles adhered thereon while performing LIBS analysis on it with accurate results.

In yet another aspect, the method and apparatus of the present disclosure relates to the use of a plurality or series of laser pulses to produce a series of measurement for real-time analysis. This provides a mechanism for closed loop feedback control of topical materials (i.e., monitoring and control of topical materials including without limitation seasoning(s) or coating(s)) and the ability to adjust a process being monitored in real-time based on the results of the analysis of a plurality of food product surfaces.

Other aspects, embodiments and features of the invention will become apparent from the following detailed description of the invention when considered in conjunction with the accompanying drawings. The accompanying figures are schematic and not intended to be drawn to scale. In the figures, each identical, or substantially similar component that is illustrated in various figures is represented by a single numeral or notation. For purposes of clarity, not every component is labeled in every figure. Nor is every component of each embodiment of the invention shown where illustration is not necessary to allow those of ordinary skill in the art to understand the invention.

BRIEF DESCRIPTION OF DRAWINGS

Various embodiments are illustrated in an exemplary manner by the accompanying drawings. The drawings and accompanying description should be understood to explain principles of the embodiments rather than be limiting. Other embodiments will become apparent from the description and the drawings.

DETAILED DESCRIPTION

Figure 1:
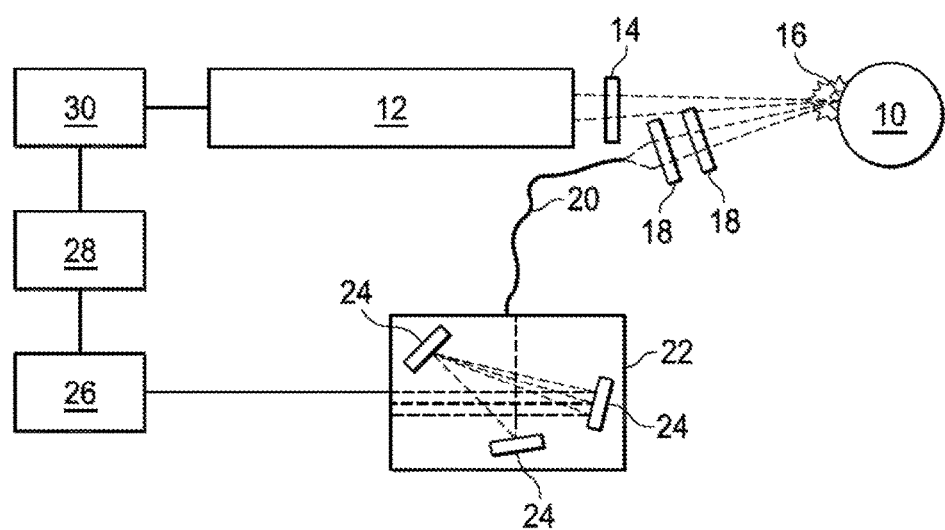
FIG. 1 is a block diagram of a typical setup for the use of LIBS on an unknown material.

FIG. 1 illustrates a typical LIBS system for the testing of an unknown material sample 10. A pulsed laser 12, powered by a power source 30, for sample ablation or breakdown is focused onto the sample 10 through a focusing lens 14 to create a plasma or spark 16. Collection lenses 18 then deliver the light from the plasma 16 to a spectrometer 22 via an optical fiber 20. The spectrometer contains therein a set of optical lenses 24, which disperses the collected lights and separates the emission peaks for elemental analysis in a detector module 26. A computer system 28 then collects the data for analysis and also helps control the precise timing of the plasma emission analysis. Characteristic atomic emission lines of the elements of the plasma can then be observed. Such analysis can provide for a determination as to whether one or more elements of interest are present in a target sample. The laser beam may last for a few microseconds and the plasma a few hundreds of microseconds, with plasma temperatures reaching an excess of 30,000 K early in its lifetime (<about 100 nsec). This plasma rapidly decays to ambient conditions; however, typically the laser pulse removes some material at an ablation site of the targeted sample.

Figure 2:
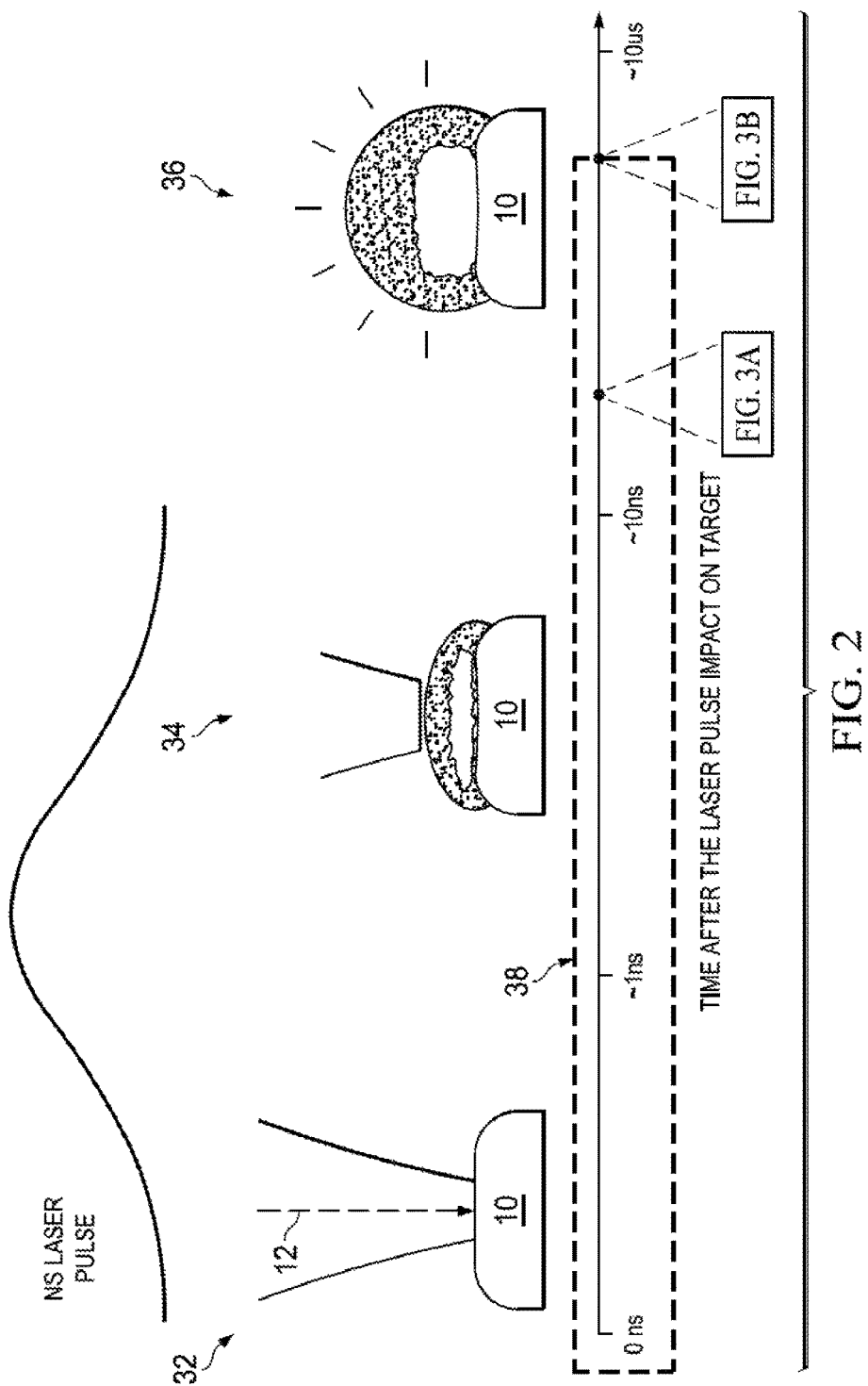
FIG. 2 illustrates the effect of a laser on a sample and formation of a plasma to be analyzed.
Figure 3A:
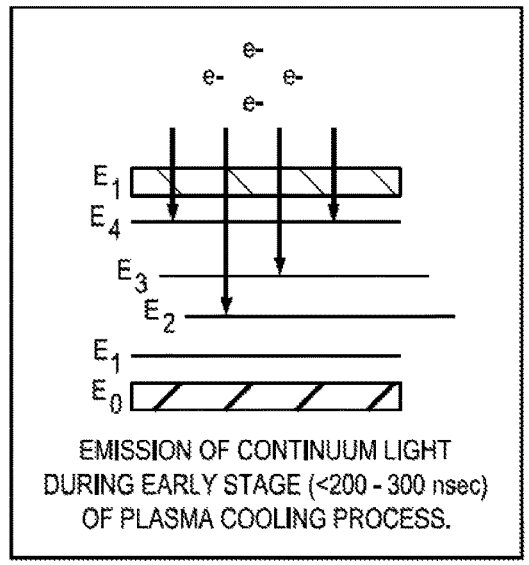
FIGS. 3A and 3B illustrate electron emission that take place during LIBS analysis.
Figure 3B:
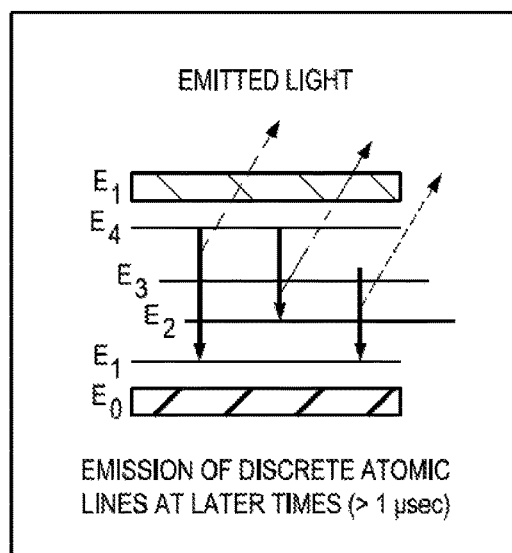

FIG. 2 illustrates a general timeline following the impact of a pulse laser on a target sample, on which generally a high temperature plasma is initiated followed by its expansion above the sample surface. The high intensity laser pulse 12 interacts with the sample 10 targeted for analysis and produces a plasma plume 34 that evolves with time from the point of impact 32. As the pulse laser impacts the surface, an energy absorption phase 34 takes place, which is typically coupled with material ejection from the surface at the ablation site. The expansion 36 of post ablation interaction plasma becomes visible with the formation of laser-supported shock waves, followed by spectroscopic emissions and recondensation of the sample. The gate delay 38 after the laser pulse impact is the delay of the LIBS spectra acquisition to improve the signal with respect to continuum background. More specifically, gate delay addresses the continuum emission that originates from kinetic energy adjustment of slowing free electrons in the presence of an electric field of ions and electron-ion recombination (shown in more detail in FIGS. 3A and 3B. In FIG. 3A is shown the emission of continuum light during early stages (<200-300 ns) of the plasma cooling process. This generates white light, which is not useful for analysis. As continuum emission decays, discrete atomic emission lines from ions can be seen in as early as a few hundreds of nanoseconds (>1 μsec), followed by the emission lines from excited atoms that are strong on a microsecond time scale (FIG. 3B). The discrete line emissions are useful for analysis and the emitted light is then collected for data acquisition. Thus, spectral emission occurs as a result of the subsequent relaxation of the constituent excited species.

In some fields, use of LIBS destroys only a very small amount of the sample material, which is ablated by the laser. However, in the field of cooked food products comprising a low moisture content (less than about 3-5% to create a shelf stable product), including food products, the use of LIBS is more difficult to achieve in light of a number of complications including the desire to prevent destruction of a ready-to-eat product before it is consumed. Destruction as used herein relates to the overall organoleptic measures or profiles of a food or drink product such as any or all of flavor, appearance, stability, and texture. The force of laser striking the surface of a crispy fried or baked product, for example, can compromise product integrity as the product undergoes heating from the ablation. Because of the importance of maintaining the structural integrity of a food product and the accuracy that LIBS methods can provide, an improved LIBS method and apparatus is desirable for use in conjunction with foods.

The proposed method for analyzing quality of a moving product material, while preserving its overall appearance (color and shape) and taste as described herein, generally comprises the steps of: moving a material under a laser induced breakdown spectroscopy system, wherein the material comprises a plurality of discrete products, each discrete product comprising a heterogeneous surface; sending a pulsed laser beam to the heterogeneous surface of the material, said laser pulses providing energy per unit area in the range of about 1.00 to 90.0 J/cm$^2$ (also known as fluence), thereby producing a plasma of material from the heterogeneous surface; transmitting optical emission generated by the plasma to a spectrum analyzer of the laser induced breakdown spectroscopy system; and analyzing a spectrum of the optical emission to determine an element of the material.

As used herein, "discrete" refers to an individually separate and distinct or detached product. In one embodiment, the plurality of discrete products comprises a high rate of variation in depth along a moving surface, as will be further discussed below. Thus, the distance between the heterogeneous surface of the product and the above spectroscopy system will vary as the material travels below it. As used herein, a heterogeneous surface is meant to refer to a food or beverage matrix comprising at least two different substances, compositions, characteristics or physical states, wherein the internal or base composition is different from the surface composition. Thus, by way of example, a heterogeneous surface may include a surface having a layer or coating of one or more substances on top of a different type of material, a surface having particles of a different substance, or two or more mixed solid substances that differ from one another by composition or some characteristic including without limitation two or more solid substances of a different particle size. In one embodiment, the one or more substances on top comprise one or more different types of seasonings on the surface of a food product. In one embodiment, the seasonings are in solid form.

In one embodiment, the targeted material for analysis is a food product. In one embodiment, the food product is a cooked food product. In one embodiment, the cooked food product is ready-to-eat and comprises a moisture content of less than about 3%. In one embodiment, the cooked food product being analyzed comprises an amount of oil within or on top thereon. In one embodiment, the heterogeneous surface comprises a three-dimensional particle layer or coating, or a plurality of three-dimensional particles. In one embodiment, the heterogeneous surface is that of a food product with a particle layer or coating, wherein the coating or layer is one or more seasoning particles having a particle size distribution. In one embodiment, the food product is a potato or potato based shelf-stable food product. In one embodiment, the element being detected is one of sodium, calcium, copper, zinc, magnesium, and potassium. In one embodiment, elements correlate to seasoning levels applied onto a food product. For example, a trace element (such as sodium) can be used to quantify the topical content of a food product. Table 1, below, indicates a few example elements and the wavelengths unique to them.

TABLE 1

| Wavelength (nm) | Element |
| --- | --- |
| 589.11 | Na |
| 510.55 | Cu |
| 636.23 | Zn |

The proposed method described herein may be applied to any number of foods, including without limitation ready-to-eat foods (whether fried, baked or microwaved), beverages, dairy products, nuts, cereals, crackers and baby foods. As used herein, a ready-to-eat food product is one in which no further cooking or preparation step is required for the food product to be readily consumed in a desirable eating experience. Thus, a ready-to-eat food product is a finished, non-intermediate product, not requiring additional processing prior to sale or consumption.

Generally, a method for elemental analysis on a moving material comprises the steps of continuously moving a material under a laser induced breakdown spectroscopy system, wherein the product comprises a heterogeneous surface; sending a laser beam to the heterogeneous surface of the material, said laser beam generating energy of between about 1.00 to about 90.0 J/cm2, thereby producing a plasma; transmitting emission generated by the plasma to a spectrum analyzer of the laser induced breakdown spectroscopy system to measure a wavelength corresponding to an element; and analyzing a spectrum of the emission to determine an amount of the element on the material. In one embodiment, the amount, for example, may be zero where a corresponding peak is not present. In other embodiments, any number of methods may be used to determine the amount of an element of interest based on the presence of a corresponding peak.

Figure 4:
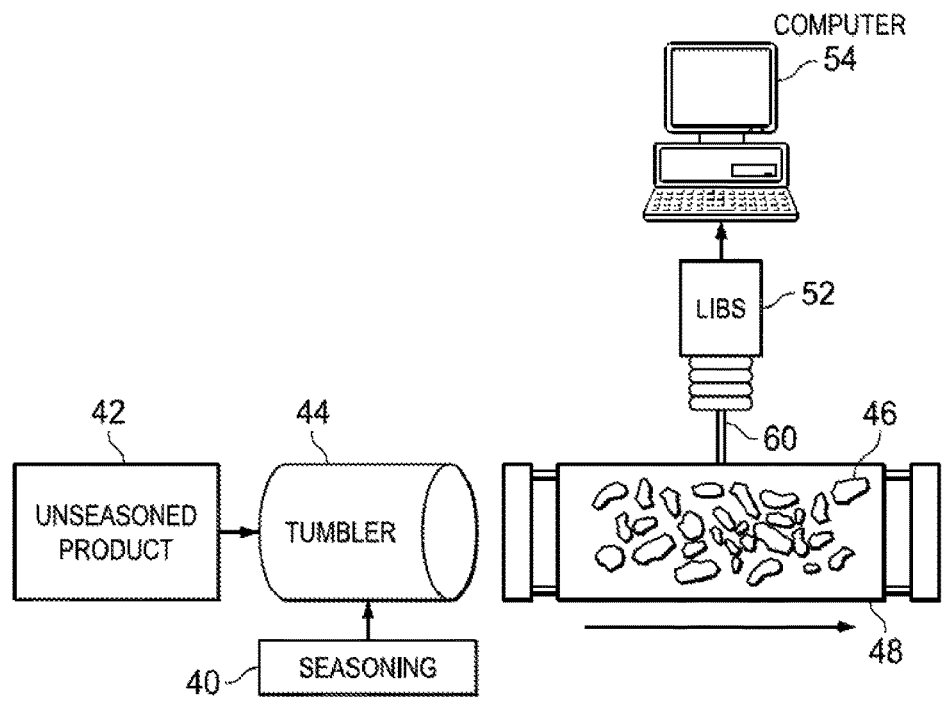
FIG. 4 illustrates the coupling of a LIBS system to a moving conveyor belt according to one aspect of the present disclosure.

FIG. 4 illustrates a general schematic for an embodiment wherein a plurality of seasoned food products 46 are subjected to LIBS analysis while being conveyed on a conveyor belt 48. More particularly, FIG. 4 shows the end of a product cooking line wherein unseasoned (yet cooked) potato slices 42 are sequentially seasoned in a tumbler 44 with seasoning 40, and transferred to a conveyor belt 48 before packaging. Thus, in one embodiment, the material undergoing analysis comprises a plurality of individual, bunched or piled products 46 randomly distributed and stacked onto the conveyor belt without regard to monolayer or organized stack-type arrangement. In practice, a plurality of products or materials 46 will substantially cover the width of a conveyor belt 48. Thus, the conveyor belt 48 may comprise a plurality of cooked and seasoned food products 46 quickly deposited onto a conveyor as in a continuous process line for mass production. The products 46 may thus comprise a variable height on the conveyor belt, meaning a variable distance from the laser 60.

Figure 5B:
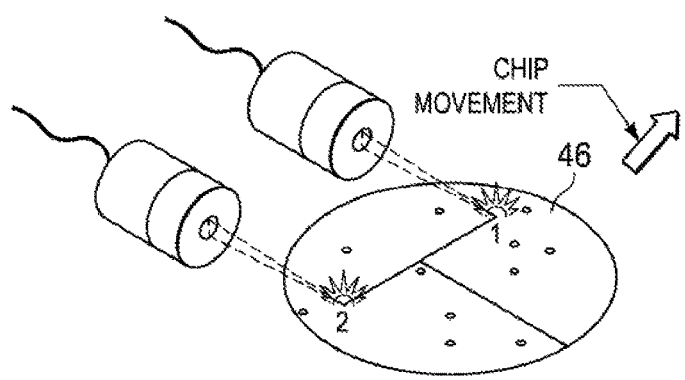
FIG. 5B illustrates the portion of a food sample targeted by a laser according to one embodiment
Figure 5A:
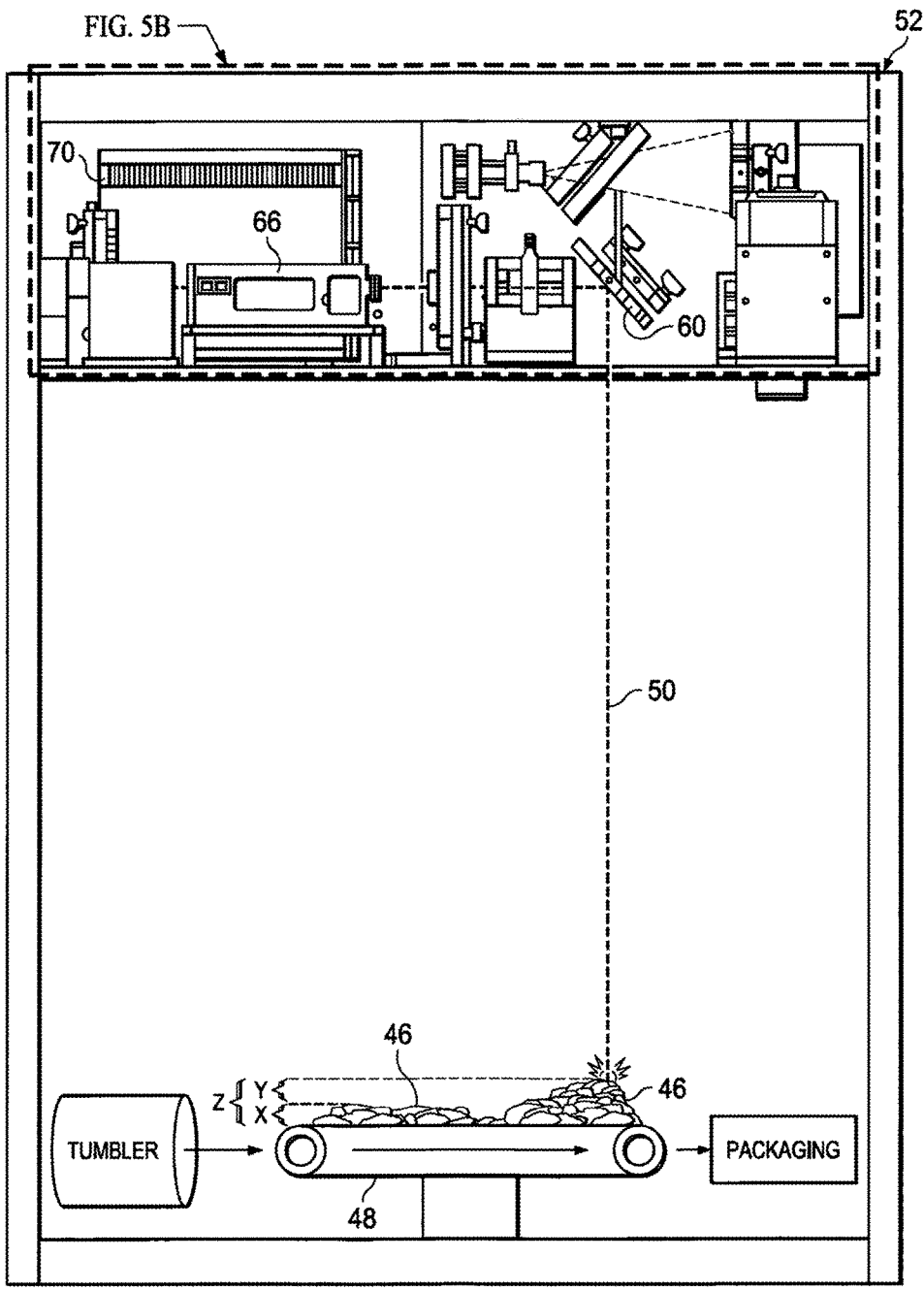
FIG. 5A illustrates the coupling of a LIBS system to a moving belt for analysis of a heterogeneous food product in one embodiment of the present disclosure.

In one embodiment, the product spans a width of about 30 to 36 inches, with a product depth that varies by +/−2 inches, as depicted in FIG. 5A. A laser beam 50 generated from a laser source 66 provides an emission from which data is obtained and sent to a computer 54 for analysis. The coupling with a LIBS system 52 as described herein allows for real-time monitoring and evaluation of a concentration of a particular element or elements on the surface of a group of randomly placed individual products (lumped together) for quality control. A material comprising a plurality of individual products 46 is moving in the direction of the arrow on a conveyor belt 48. As product 46 is conveyed downstream on the conveyor belt 48, it passes under a LIBS system 52, which focuses a laser beam 50 from the laser source 66 down onto the moving product 46. Thus, in one embodiment, the moving step comprises the conveyance of the material on a conveyor belt as the material goes from one step to the next in a product line. The conveyor comprises a moving rate of not more than 65 feet per minute in one embodiment. In one embodiment, the conveyor moves at between about 15 to about 45 feet per minute. A LIBS system can be disposed above the conveyor ablation site to collect plasma light from the laser beam in a top light collection configuration. In one embodiment, the LIBS system comprises a series of optical elements or mirrors configured to provide a long laser light beam path length before reaching the surface of a product below, as shown in FIG. 5B. In one preferred embodiment, the mirror configuration preferably can redirect the laser light path to effectuate a wide focusing depth of at least +/−2 inches around the impact site. Furthermore, an embodiment can effectuate a relatively wider focusing depth of about 4 inches using the mirror configuration. A wide focusing depth allows for a more accurate focus of the laser onto an average height of the products as described herein. Collected light is sent to a spectrometer for measurement by way of an optical fiber cable, which communicates the data from the spectrometer to a detector module 70. A power supply (not shown) provides power to the laser and/or an external computer. Optionally, a viewing camera or tv monitor (not shown) may also form part of the system for viewing the sample and laser spot placements.

As evident by the distances marked x and y in FIG. 5A, and as described above, there is variability to the height or depth (i.e., product bed) of the material as it sits on the conveyor belt. For example, in one embodiment, the chip height z may be no less than 3 inches. In one embodiment, the chip height z is between about 1.5 to about 5 inches. In one embodiment, the distance from the laser source is about 14 inches.

FIG. 5B depicts a close-up image of a moving seasoned food product targeted by a laser, depicting laser ablation sites 1 and 2, which may sequentially strike the product at laser ablation sites 1 and 2 as the product moves in the direction shown by the arrow along a conveyor belt 48. It should be noted that the product 46 of FIG. 5B assumes a perfectly flat food element, which is not always possible depending on the cooking methods employed to the finished food product. In practice, the laser may not hit the same or similar spot in each and every moving product due to the variance of height z. Consequently, in one embodiment, a specific field of the moving material or product bed should be targeted to provide more accurate results and to address the variability of the height z. The targeted field can be defined as the location where the diameter of the laser light is at a minimum or the range between a) the ratio of minimum detectable distance to a predetermined distance and b) the ratio of the maximum detectable distance of detectability to the predetermined distance.

Figure 6:
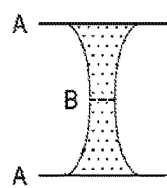
FIG. 6 illustrates the fluence of a laser according to one embodiment of the present disclosure.

FIG. 6 depicts the laser fluence ($J/cm^2$), which is configured to deliver a height window of less than or equal to half the fluence at the average height of the products, or about a 50% reduction in fluence at extreme ends A. One skilled in the art, armed with this disclosure, can determine the necessary optics configuration to arrive at the required fluence in accordance with the specific product to be analyzed. In one embodiment, the laser targets a height window of the plurality of products within +/−2 inches of the average height of the products. In one embodiment, the laser targets a height window of the plurality of products within 4 inches of the average height of the products. In one embodiment, the laser targets a height window of between about 2-6 inches. In one embodiment, the laser targets a height window of about 4 inches.

In one embodiment, the use of LIBS to send a laser beam onto a surface of a food product avoids flavor loss or a change in oil quantity with the assistance of a low energy laser. The low energy of the laser helps ensure that the material or plurality of materials remains substantially unchanged and in no way negatively impacted in terms of taste, texture, color or size (i.e., product integrity and stability). The LIBS system disclosed herein can be applied using a variety of different types of lasers operable to emit energy and/or fluence within the disclosed values. In one embodiment, the laser used with the present method and apparatus is a diode pumped laser. In one embodiment, the ratio of the spot size to size of particle of interest ranges from about 1:2 to about 2:1.

Figure 8:
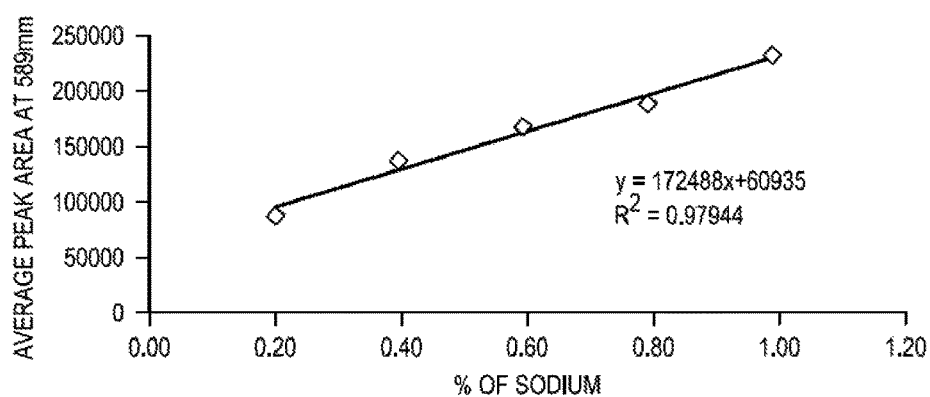
FIG. 8 illustrates a calibration curve for a sodium percentage on the surface of a plurality of food products.
Figure 7:
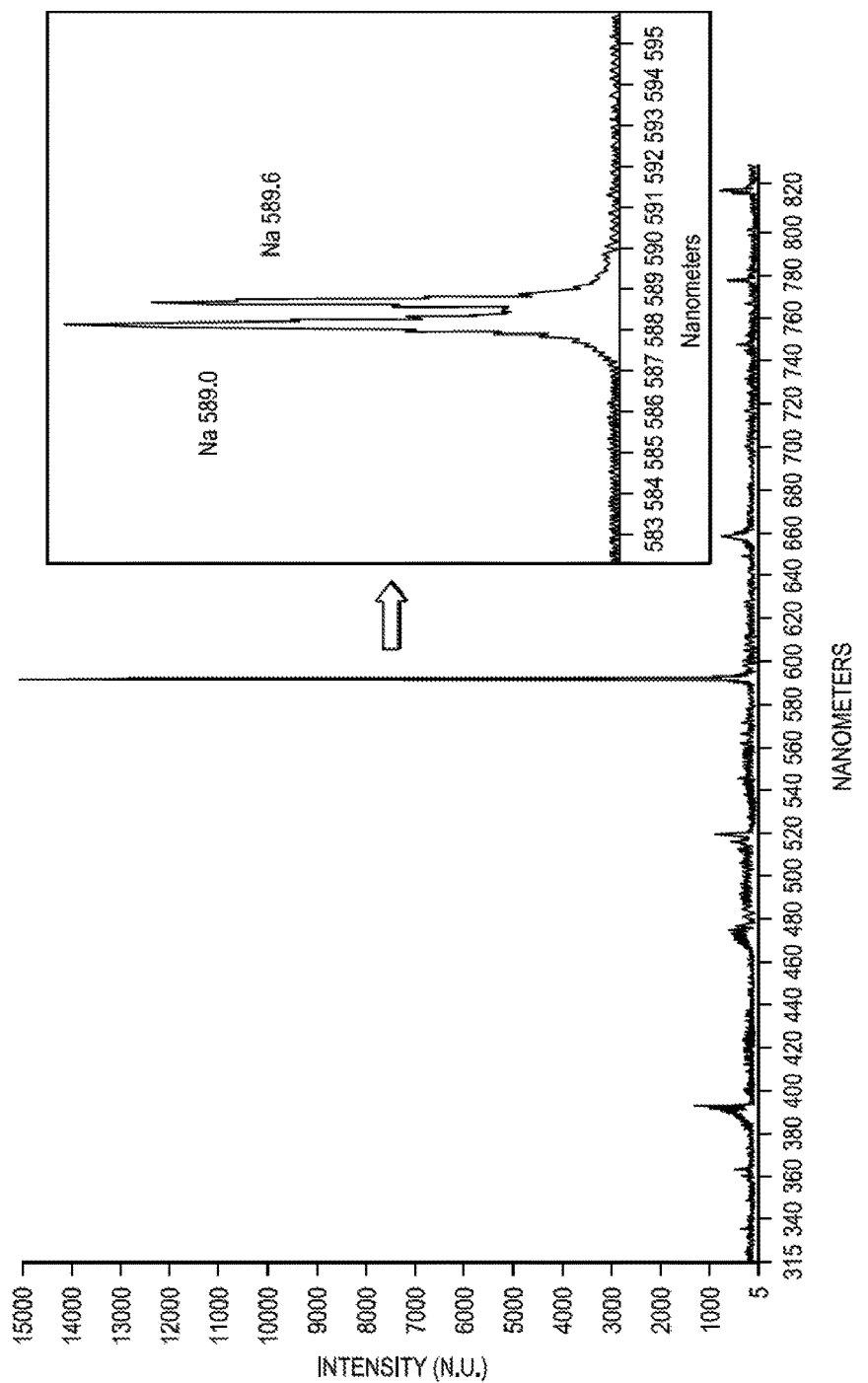
FIG. 7 illustrates a graphical representation of a LIBS spectrum of an element on a moving food product.

FIG. 7 illustrates a graphical representation of a LIBS spectrum of sodium on a moving food product surface. The concentration of an element of interest in the sample material can be determined in one embodiment by comparing the measured intensity of the elemental spectral line with that of a working calibration curve as shown in FIG. 8, which measures a percentage concentration of sodium from a plurality of food products. This calibration curve is obtained by performing LIBS measurements on a sample for which concentration is known. To ensure reliability of the calibration procedure, several standard samples were analyzed for each concentration using a mettler titration reference method. Table 2, below, notes the values of the plotted points in FIG. 8.

TABLE 2

| % Na | Avg Peak Area |
|---|---|
| 0.20 | 87173.2383 |
| 0.39 | 138308.0506 |
| 0.59 | 167765.5345 |
| 0.79 | 188590.2997 |
| 0.98 | 231503.5276 |

Thus, linear regression may be used in one embodiment to determine the percentage of sodium in a batch of moving discrete products based on the average peak at 589 nm, which is the wavelength at which sodium atoms emit light. This provides a line that yields concentration by weight of the material corresponding to a given intensity of the associated specific elemental line. In one embodiment, for example, approximately 150 to 250 grams of sample are collected from a batch being analyzed on a conveyor belt prior to packaging. About 150 grams of pulled sample can be ground to evenly disperse the salt throughout the sample. In one embodiment, samples can be pulled from a product line every half hour for multiple points in using linear regression, if desired.

Generally, any method of analyzing features of produced peaks may be used. For example, analysis may comprise any number of methods related to how thick the peak is, the area of the peak, how tall the peak is, etc. Multivariate processing such as a standard multivariate analysis may be used in one embodiment. Correlations may be made to known levels of elements of a surface on a material, as further described below. Average size particles of particles on a surface or distance from the laser may also be taken into account. Any number of these features may be incorporated into an algorithm or computer for quick analysis. During continuous or dynamic production lines, one skilled in the art armed with this disclosure can determine how to control or configure a closed loop feedback control system to raise or lower an amount of an element as desired. For example, should the amount of sodium be calculated below a targeted amount during production, additional sodium can be introduced into the production line to attain the targeted amount. Similarly, if sodium levels are above a targeted amount, less sodium can be used for seasoning the plurality of food products.

Generally, any method of distinguishing background from the moving food products known in the art may be used with the method described herein. For example, in one embodiment, multivariate image analysis known as Principle Component Analysis (PCA) (as described in U.S. Pat. No. 7,068,817 issued to Bourg, et al.) is applied to the image to distinguish the background. In one embodiment, the method may comprise a partial least squares regression analysis. In one embodiment, the method may comprise Partial Least Squares Discriminant Analysis (PLS-DA). In one embodiment, vector quantization such as k-means clustering may be used. To identify successful laser shots from a series of laser beams analyzing a plurality of moving products, statistical hypothesis tests may be applied, such as the Ljung-Box test, in one embodiment for white noise. The Ljung-Box Q-test is a more quantitative way to test for autocorrelation at multiple lags jointly. It is a type of statistical test of whether any of a group of autocorrelations of a time series are different from zero. Instead of testing randomness at each distinct lag, it tests the "overall" randomness based on a number of lags. The null hypothesis for this test is that the first m autocorrelations are jointly zero. Successful shots may thus be defined as those shots with a p-value of identically 0 for the test. One skilled in the art, armed with this disclosure, may combine any software capable of using these methods in conjunction with a LIBS system described herein.

Figure 9:
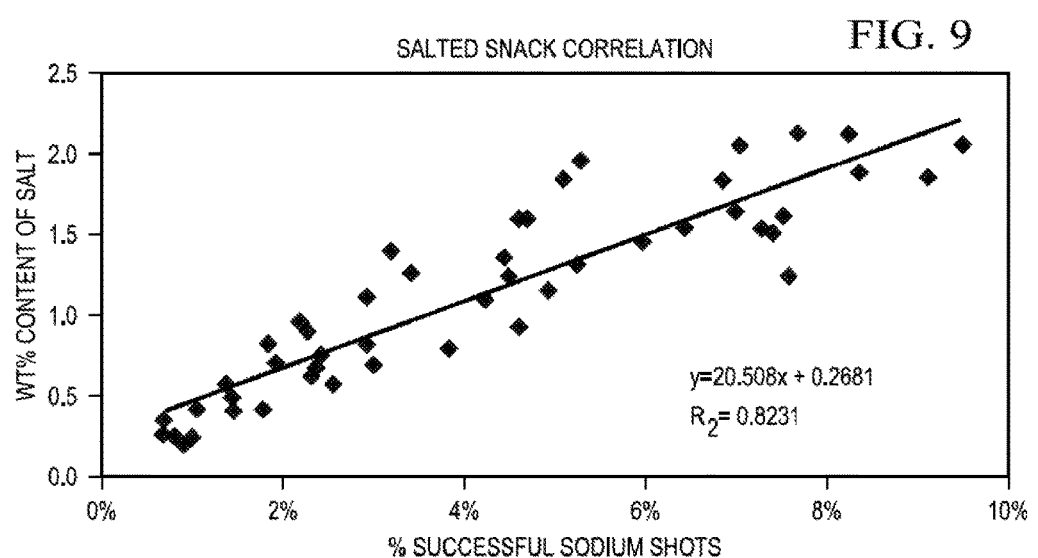
FIG. 9 is a graph of weight percent salt measured analytically against the percentage of successful sodium shots.

FIG. 9 depicts a correlation graph obtained for detecting sodium on a salted food product and more specifically, by modeling weight percent salt measured analytically again percent successful sodium shots. A successful sodium shot is defined as a spectral response sufficiently above noise commonly described as some factor of the variance of noise or "detection limit." A total of 48 samples were analyzed for this model. Unsalted base snack foods used to produce salt range samples were collected from 2 different production facilities and spanned 5 different raw material varieties. This variability incorporates real world variability for online measurement and thereby reduces risk of over-fitting. Sodium chloride was applied at target levels ranging from 0.2% to 2.0%. Each sample was analyzed (shot at) 5,000 times with the sample being moved relative the laser to avoid analyzing the same point twice. The samples were presented to the laser in a manner simulating online production. The laser was never able to contact the bottom of the container, but the product presentation had variable height (+/−2 inches) relative to the laser source as it was moved around as previously described.

An apparatus for analyzing moving surfaces, according the present disclosure, thus comprises a moving surface for holding a material to be analyzed, the material comprising a heterogeneous surface; a sensing unit positioned over the moving surface, the sensing unit comprising: a laser capable of emitting a laser beam for contact to the heterogeneous surface of the materials, said laser generating energy of between about 150 to about 900 $mJ/mm^2$; an optics configuration for collecting and delivering light from the laser beam contact with the heterogeneous surface to a spectrometer; and a displacement sensor in communication with the optics. The moving surface may comprise, for example, a conveyor belt system or moving platform for the material. In one embodiment, the material to be analyzed comprises a plurality of discrete food products bunched on the moving surface. In one embodiment, the optics configuration produces a height window that delivers a minimum of half the fluence to a targeted portion of the plurality of discrete food products. In one embodiment, a computer in communication with the spectrometer analyzes a spectrum of an element, produced by the laser ablation on the surface of the material or heterogeneous surface of a food product.

The LIBS system described herein can be applied to any number of food or beverage manufacturing process lines, including without limitation baked or fried potato chip lines. Seasoned baked chips can be subjected to LIBS as described herein for analysis of the concentration(s) of any number of elements. The data can also be used in a closed loop to eject one or more materials having a value above a submitted threshold of concentration. A product abort mechanism can be combined with the system described herein to adjust the overall element concentration to a more precise value or range for a batch of products. Thus, the real-time elemental data produced by the methods described above can be used by operators to either make manual adjustments to the seasoning step(s) of the product line and/or advanced multivariate control strategy to automatically adjust the level of an element such as sodium of a food product.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. In the above discussion and the below claims, the term "comprising" is open-ended, meaning it should be interpreted to mean "including but not limited to."

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention.

Accordingly, the foregoing description and drawings are by way of example and illustration only.

In the foregoing specification, various aspects are described with reference to specific embodiments, but those skilled in the art will recognize that further aspects are not limited thereto. Various features and aspects described above may be used individually or jointly. Other aspects of the invention, including alternatives, modifications, permutations and equivalents of the embodiments described herein, will be apparent to those skilled in the art from consideration of the specification, study of the drawings, and practice of the various aspects. Further, various aspects can be utilized in any number of environments and applications beyond those described herein without departing from the broader spirit and scope of the description. The written description and accompanying drawings are, accordingly, to be regarded as illustrative rather than restrictive.

Although various embodiments have been presented and explained using simplified examples, it will be understood that various changes and modifications are possible with regard to materials, shapes, and dimensions, without departure from the scope of the patent claims. The embodiments and preferred features described above should be considered exemplary, with the invention being defined by the appended claims, which therefore include all such alternatives, modifications, permutations and equivalents as fall within the true spirit and scope of the present disclosure.

What is claimed is:

1. A method for elemental analysis of moving material, the method comprising the steps of:
   continuously moving the material under a laser induced breakdown spectroscopy system, wherein the material comprises a heterogeneous surface; and wherein the material is a plurality of solid products comprising a structural integrity and the heterogeneous surface comprises a plurality of particles adhered on the solid products, the solid products being dissimilar from the particles;
   sending a pulsed laser beam to the heterogeneous surface of the material, wherein each laser beam pulse provides an energy in the range of about 1.00 to 90.0 $J/cm^2$, thereby ablating small amounts of the heterogeneous surface and producing a plasma of material from the heterogeneous surface;
   transmitting optical emission generated by the plasma to a spectrum analyzer of the laser induced breakdown spectroscopy system to measure a wavelength corresponding to an element; and
   analyzing a spectrum of the emission to determine an amount of an element in the heterogeneous surface, said method preserving the structural integrity of the plurality of solid products and the particles adhered on the solid products.

2. The method of claim 1 wherein the heterogeneous surface comprises a plurality of particles on a food product, wherein the particles are dissimilar from the food product.

3. The method of claim 1 wherein the products include a plurality of different food products.

4. The method of claim 3 wherein the food products are cooked.

5. The method of claim 1 wherein the solid products are food products, the laser pulses are operable to ablate small amounts of the heterogeneous surface without destruction, and the optical emission generated by the plasma is used to determine one or more elements on the heterogeneous surface of the food products.

6. The method of claim 1 wherein the solid products comprise a plurality of discrete products and optical emission generated by the plasma is used to determine one or more elements on different discrete products.

7. The method of claim 6 wherein the element is sodium.

8. The method of claim 6 wherein the element is selected from the group consisting of calcium, copper, zinc, magnesium, and potassium.

9. The method of claim 1 wherein the solid products comprise heterogeneous surfaces of a plurality of food products having variable height, and further comprising the step of quantifying a concentration of the element in the heterogeneous surfaces of different food products.

10. The method of claim 9 further comprising the step of calibrating the concentration by using a calibration curve established on samples comprising a known concentration of the element.

11. The method of claim 1 wherein the laser beam comprises a ratio of spot size to size of particle of from about 1:2 to about 2:1.

12. The method of claim 1 comprising a gate delay of up to about 10 microseconds.

13. An apparatus operable to analyze heterogeneous surfaces of moving food products without destruction, wherein each heterogeneous surface comprises a plurality of particles adhered to a portion of a respective food product, the apparatus comprising:
  a movable surface operable to move the food products; and
  a sensing unit positioned over the movable surface;
wherein:
  the sensing unit comprises a LIBS system operable to direct a laser beam having a fluence of between about 150 to about 900 $mJ/mm^2$ onto each heterogeneous surface;
  the laser beam is operable to generate a light emitting plasma through the laser beam contact with the heterogeneous surface; and
  the LIBS system comprises an optics configuration operable to collect and deliver the light emitted from the plasma to a spectrometer, and a displacement sensor in communication with the optical configuration;
  and the laser beam is operable to maintain the structural integrity of the food products.

14. The apparatus of claim 13 wherein the food products comprise a plurality of discrete food products bunched on the movable surface.

15. The apparatus of claim 14 wherein the optics configuration produces a height window that delivers a minimum of half the fluence to a targeted portion of the plurality of discrete food products.

16. The method of claim 1 wherein the solid products are consumable and the elemental analysis is non-destructive.

* * * * *